United States Patent [19]

Messina et al.

[11] Patent Number: 5,026,866
[45] Date of Patent: Jun. 25, 1991

[54] SYNTHESIS OF 2,2'-BIS-Δ²-OXAZOLINE

[75] Inventors: Giuseppe Messina, Alghero; Loreno Lorenzoni, Porto Torres; Giovanna Chessa, Sassari, all of Italy

[73] Assignee: Enichem Anic S.p.A., Palermo, Italy

[21] Appl. No.: 454,407

[22] Filed: Dec. 21, 1989

[30] Foreign Application Priority Data

Dec. 23, 1988 [IT] Italy ................................ 23100 A/88

[51] Int. Cl.⁵ .......................................... C07D 263/08
[52] U.S. Cl. .......................................... 548/238; 558/6
[58] Field of Search ....................... 548/238, 239, 237

[56] References Cited

FOREIGN PATENT DOCUMENTS

| | | | |
|---|---|---|---|
| 3310905 | 9/1984 | Fed. Rep. of Germany | 548/238 |
| 0133276 | 10/1981 | Japan | 548/238 |
| 0032869 | 2/1983 | Japan | 548/238 |
| 0134084 | 8/1983 | Japan | 548/238 |
| 0065084 | 4/1984 | Japan | 548/238 |
| 0065085 | 4/1984 | Japan | 548/238 |

*Primary Examiner*—Donald G. Daus
*Attorney, Agent, or Firm*—Hedman, Gibson, Costigan & Hoare

[57] ABSTRACT

The present invention relates to a new method of synthesis of 2,2'-bisΔ²-oxazoline, which consists of three steps:

in the first step,
N,N'-bis-(2-hydroxyethyl)-oxamide (I) is reacted with hydrogen chloride and a nitrile of formula RCN in which R=H, alkyl, aryl, arylalkyl, alkylaryl, in order to yield the corresponding N,N'-bis-(2-iminoacyloxyethyl)oxamide.2HCl     (II).

In the second step, the compound (II) is pyrolyzed in order to yield
N,N'-bis-(2-chloroethyl)oxamide (III) which in the third step generates, by means of the treatment with a base, the desired product 2,2'-bis-Δ²-oxazoline.

8 Claims, No Drawings

SYNTHESIS OF 2,2'-BIS-Δ²-OXAZOLINE

The present invention relates to a new method of synthesis of 2,2'-bis-Δ²-oxazoline, which method consists of three steps:

in the first step,

N,N'-bis-(2-hydroxyethyl)-oxamide (I) is reacted with hydrogen chloride and a nitrile of formula RCN in which R = H, alkyl, aryl, arylalkyl, alkylaryl, in order to yield the corresponding N,N'-bis-(2-iminoacyloxyethyl)oxamide.2HCl (II).

In the second step, the compound (II) is pyrolysed in order to yield

N,N'-bis-(2-chloroethyl)oxamide (III) which in the third step generates, by means of the treatment with a base, the desired product 2,2'-bis-Δ²-oxazoline.

2,2'-bis-Δ²-oxazoline is a compound having a structure endowed with characteristics of high reactivity towards carboxylic functions and can be both used as a chain lengthening agent for polymers having carboxylic functions at their chain ends, and as a coupling agent for carboxylic compounds.

In particular, 2,2'-bis-Δ²-oxazoline is used in the processes of synthesis of polyesters, polyamides and polyester-polyamide resins.

At present, the precursor of 2,2'-bis-Δ²-oxazoline, N,N'-bis-(2-chloroethyl)-oxamide (III), is prepared at the industrial level by means of the chlorination with hydrogen chloride of N,N'-bis-(2-hydroxyethyl)-oxamide (I) in an organic, hydrophobic solvent (JP 56071-051), or in a solvent of amidic type (JP 56083456), or also in a solvent of phenolic type (JP 56108746), anyway always at very high temperatures, comprised within the range of from 150° C. to 220° C.

When one works under these conditions, he is obliged to use an excess of hydrogen chloride owing to the poor solubility of this gas in the reaction medium at so high temperatures.

Furthermore, high-boiling solvents, expensive solvents have to be used, which require expensive treatments in order to be recovered and re-used.

The present Applicant has found now a novel route for the synthesis f 2,2'-bis-Δ²-oxazoline, wherein the precursor N,N'-bis-(2-chloroethyl)-oxamide III is obtained by means of the reaction of N,N'-bis-(2-hydroxyethyl)-oxamide (I) with hydrogen chloride and with a nitrile of formula RCN in which R=H, alkyl, aryl, arylalkyl, alkylaryl, in order to yield an N,N'-bis-(2-iminoacyloxyethyl)-oxamide.2HCl, which is pyrolysed in order to yield the compound (III).

The process is schematically shown in the following diagram, and R is preferably selected from the group consisting of H, methyl, ethyl, propyl, butyl, pentyl, hexyl, benzyl, phenyl, 2,4-dimethyl-phenyl, ethyl-phenyl, methyl-phenyl.

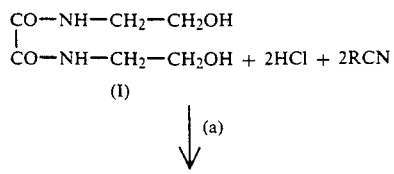

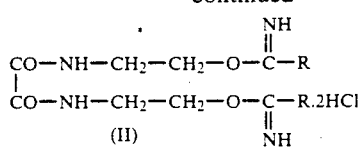

↓ (b)

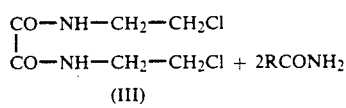

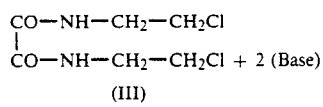

↓ (c)

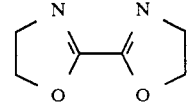

The first step is carried out under an inert atmosphere obtained by means of, e.g., a stream of anhydrous nitrogen, air or argon, at a temperature comprised within the range of from −10° C. up to 80° C. and under a pressure comprised within the range of from 1 to 15 atm.

In particular, at low temperatures hydrogen chloride will show a higher solubility and therefore the reaction can be carried out at a not very high pressure; if, on the contrary, the rection temperature is high, with increasing pressure values a high enough solubilization of the acid will be obtained as well. For example, the reaction can be carried out under room pressure, and at temperatures of round 0° C.

An amount of hydrogen chloride is used, which is from 5 to 20 times as large as the amount required by the stoichiometry of reaction, and preferably is of from 7 to 10 times as large as that amount.

The molar ratio of the nitrile to N,N'-bis-(2-hydroxyethyl)-oxamide is at least equal to the stoichiometric ratio, and is preferably higher than, or equal to, 15.

The reaction can also be carried out with a large excess of nitrile which, whenever possible, is simultaneously used as a solvent.

As an alternative, the reaction can also be carried out in an inert solvent.

In the reaction medium, the nitrile RCN and (I) are placed into contact with each other, and then hydrogen chloride is bubbled through the reaction mixture at such a flowrate as not to cause the mass to be overheated up to a temperature value exceeding the preselected temperature.

The product which is formed in the reaction, i.e., the

N,N'-bis-(2-iminoacyloxyethyl)-oxamide.2HCl (II), precipitates as a solid product from the solution of reaction. These compounds, which are represented by the general formula:

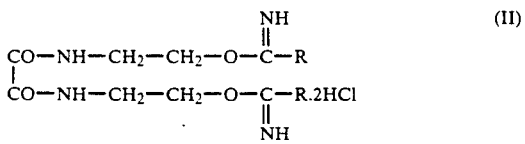

are new, and constitute a subject-matter of the instant invention as well.

Their structure was characterized by elemental analysis, N.M.R. analysis and I.R. analysis.

These products are recovered from the reaction medium by removing the solvent by distillation or filtration. The second method is preferred, and the filtrate constituted by the solvent and/or nitrile saturated with hydrogen chloride can be recycled as such, after the suitable addition of fresh solvent and the replenishment of consumed hydrogen chloride, contrarily to what happens in the hereinabove disclosed prior art in which, owing to water formation, the solvent has to be thoroughly dehydrated before being re-used.

In the second step of the process according to the present invention, N,N'-bis-(2-iminoacyloxyethyl)-oxamide.2HCl is pyrolysed at a temperature comprised within the range of from 120° C. to 200° C., and preferably comprised within the range of from 140° C. to 170° C., in the absence of solvents, or in a high-boiling paraffin, in which the compound (II) is kept suspended by stirring. The pyrolysis is nearly immediate, and in the first case a light-coloured solid is recovered from which the amide

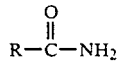

formed as a byproduct, is removed by vacuum distillation or water washing, whilst, in case the reaction was carried out in high-boiling paraffin, the by-product

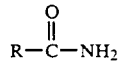

is removed by high-temperature filtration and then by cooling the precipitation is obtained of N,N'-bis-(2-chloroethyl)-oxamide, which is isolated in its turn by filtration. In both cases, the yield is of about 80%.

The so obtained product does not require any further processes of purification. Therefore, other processing steps dedicated to the recovery and purification of crystallization solvents are avoided.

In the last reaction step, N,N'-bis-(2-chloroethyl)-oxamide is refluxed in methanol, with a base selected from the group consisting of NaOH, KOH, MeONa, EtONa, and preferably potassium hydroxide, in a molar ratio at least equal to the stoichiometric value, for 1 hour.

At the end the separated alkali-metal halide is filtered off and the methanolic solution is evaporated, with 2,2'-bis-$\Delta^2$-oxazoline being obtained as a solid, which is then purified by means of known techniques.

In case the reaction of thermal breakdown has been carried out in a high-boiling paraffin, the reaction of cyclization can be carried out on the same paraffinic suspension as this latter is obtained at the end of the pyrolysis, and which contains hence both N,N'-bis-(2-chloroethyl)-oxamide and the byproduct RCONH$_2$, in the molar ratio of 1:2. To this suspension methanol is added together with a base selected from among those above mentioned, preferably potassium hydroxide. The amount of base which is used is at least the same amount as required by the stoichiometry of the reaction of cyclization, plus an amount at least equimolecular relatively to RCONH$_2$ byproduct.

The reaction mixture is heated up to methanol refluxing temperature for about 1 hour, and then both the paraffinic phase and the alkali-metal halide are removed, the first one by phase separation, and the second one by filtration. The methanolic solution is then treated as disclosed hereinabove.

EXAMPLE 1

28 g (159 mmol) of N,N'-bis-(2-hydroxyethyl)-oxamide and 94 g (2.29 mol) of anhydrous acetonitrile are charged under a nitrogen blanketing atmosphere to a three-necked reactor of 200 cc of capacity equipped with thermometer, gas bubbling fitting, condenser and magnetic-drive stirrer.

The reaction mixture is cooled down to 0° C. and then 80.2 g (2.2 mol) of anhydrous hydrogen chloride gas is bubbled through it at a flowrate of 820 ml/minute.

When the addition of the acid is ended, acetonitrile and the excess of hydrogen chloride are distilled off.

52.64 g (159 mmol) of N,N'-bis-(2-iminoacetate-ethyl)-oxamide.2HCl is obtained as a white solid.

Elemental analysis:
$C_{10}H_{20}N_4O_4Cl_2$
Found : C: 36.24%; H: 6.29%; N: 16.67%
Computed: C: 36.26%; H: 6.04%; N: 16.92%
$^1$-NMR Analysis (hexadeuterated DMA): δ2.45–2.65 (m 3H) 3.1–3.9 (m, 4H); 4.31–4.69 (m, 1H); 9 (m, 1H).
I.R. Analysis (KBr): 3348 cm$^{-1}$; 2922 cm$^{-1}$; 1662 cm$^{-1}$.

N,N'-bis-(2-iminoacetate-ethyl)-oxamide.2HCl is pyrolised in the absence of solvents at 170° C. The reaction of pyrolysis takes place immediately after the melting of the solid product. A slightly brown-coloured pyrolysis product is obtained, which is cooled, ground into a powder and poured into 500 ml of hot water. By filtration, 26.88 g (126 mmol) of N,N'-bis-(2-chloroethyl)-oxamide with a melting point of 200°–203° C. is recovered.

EXAMPLE 2

28 g (159 mmol) of N,N'-bis-(2-hydroxyethyl)-oxamide and 94 g (2.29 mol) of anhydrous acetonitrile are charged under a nitrogen blanketing atmosphere to a three-necked reactor of 200 cc of capacity equipped with thermometer, gas bubbling fitting, condenser and magnetic-drive stirrer.

The reaction mixture is cooled down to 0° C. and then 80 g (2.2 mol) of hydrogen chloride gas is bubbled through it at a flowrate of 820 ml/minute.

When the addition of the acid is ended, hydrogen chloride and the excess of acetonitrile are distilled off.

52.64 g (159 mmol) of N,N'-bis-(2-iminoacetate-ethyl)-oxamide.2HCl is obtained.

N,N'-bis-(2-iminoacetate-ethyl)-oxamide.2HCl is suspended in 400 ml of isododecane.

The so obtained slurry is heated up to the temperature of 155° C.

At such a temperature, the sudden disappearance of N,N'-bis-(2-iminoacetate-ethyl)-oxamide.2HCl is observed, and a fluid phase insoluble in isododecane is simultaneously formed.

From the paraffinic phase, removed from the reaction medium, 25 g (127 mmol) of

N,N'-bis-(2-chloroethyl)-oxamide with a melting point of 200°–203° C. is separated by cooling and is subsequently recovered by filtration.

The phase insoluble in isododecane contains 13.84 g of acetamide.

EXAMPLE 3

20 g of N,N'-bis-(2-hydroxyethyl)-oxamide and 312 g of anhydrous acetonitrile are charged under a nitrogen blanketing atmosphere to a three-necked reactor of 200 cc of capacity equipped with thermometer, gas bubbling fitting, condenser and magnetic-drive stirrer.

The reaction mixture is cooled down to 0° C. and then 80.2 g of anhydrous hydrogen chloride gas is bubbled through it at a flowrate of 820 ml/minute.

When the addition of the acid is ended, acetonitrile and the excess of hydrogen chloride are distilled off.

After distilling off the two reactants, 200 ml of paraffin is added to the residue, and the reaction mass is heated to 140° C. and is kept at this temperature for 1 hour, with strong stirring. The reaction mass is then cooled down to 50° C., and 25 g of KOH and 200 ml of methanol are added to it. The reaction mixture is refluxed for 1 hour. Af the end of the refluxing time, both potassium chloride and the paraffinic phase are removed—i.e., the first one by filtration and the second one by phase separation—, and the so isolated methanolic solution is evaporated. A reddish-coloured solid is obtained.

This solid product is collected with 200 ml of methylene chloride and 10 ml of water.

A clear, double-phase system is obtained, from which the organic phase is separated. The separated organic phase is desiccated over $Na_2SO_4$ and is evaporated, in order to yield 10.73 g of 2,2'-bis-$\Delta^2$-oxazoline.

We claim:

1. Process for the synthesis of 2,2'-bis-$\Delta^2$-oxazoline comprising the steps of:
   (a) reacting N,N'-bis-(2-hydroxyethyl)oxamide (I) in an anhydrous inert liquid environment, with gaseous hydrogen chloride and acetonitrile, the amount of HCl being from 5 to 20 times the stoichiometrically necessary amount, the molar ratio of acetonitrile to the oxamide(I) being greater than 15:1, at a temperature of from −10° C. to 80° C., to form the corresponding hydrochloride N,N'-bis(2-iminoacyloxy).2HCl(II); optionally
   (b) slurrying the compound (II) in a liquid paraffin;
   (c) heating the compound (II) from step (a) or the optionally slurried compound (II) from step (b) to a temperature of from 120° C. to 200° C. to convert the compound (II) into N,N'-bis(2-chloroethyl)$_2$oxamide (III), and
   (d) cyclizing the compound (III) in methanol, at the refluxing temperature and in the presence of a catalyst selected from sodium hydroxide, sodium methoxide and sodium ethoxide, the molar ratio of the catalyst to the compound (III) being at least stoichiometric.

2. Process according to claim 1, wherein the step (a) is carried out under a pressure comprised within the range of from 1 to 15 atm.

3. Process according to claim 1, wherein the reaction is carried out at a temperature comprised within the range of from 0° C. to room temperature, and under the atmospheric pressure.

4. Process according to claim 1, wherein an amount of hydrogen chloride is used, which is from 7 to 10 times as large as the stoichiometric amount, and the molar ratio of the acetonitrile to N,N-bis(2-hydroxyethyl)-oxamide is higher than, or equal to, 15.

5. Process according to claim 1, wherein the (b) step is carried out in the absence of solvents, or in a high-boiling paraffin.

6. Process according to claim 5, carried out at a temperature comprised within the range of from 140° C. to 170° C.

7. Process according to claim 1, wherein the reaction is directly carried out on the paraffinic suspension deriving from the (b) step and containing N,N'-bis-(2-chloroethyl)-oxamide and $RCONH_2$, with an amount of base at least equal to the amount required by the stoichiometry of the reaction of cyclization, plus an at least equimolecular amount of relatively to $RCONH_2$.

8. Process according to claim 1, wherein the base used is KOH.

* * * * *